United States Patent [19]

Suwa et al.

[11] Patent Number: 4,827,074
[45] Date of Patent: May 2, 1989

[54] METHOD OF THERMALLY DECOMPOSING HYDROCARBON AND THERMAL DECOMPOSITION TUBE

[75] Inventors: Akio Suwa; Nobuhisa Akiyoshi, both of Ichihara, Japan

[73] Assignee: Idemitsu Petrochemical Co., Ltd., Tokyo, Japan

[21] Appl. No.: 179,409

[22] Filed: Apr. 8, 1988

[51] Int. Cl.$^4$ .............................................. C07C 4/02
[52] U.S. Cl. ....................................... 585/648; 165/177; 165/179; 165/184; 422/202; 585/650
[58] Field of Search ................ 585/648, 650; 165/184, 165/177, 179; 422/202

[56] References Cited

U.S. PATENT DOCUMENTS 2,864,591 12/1958 Frink .................................... 165/177

FOREIGN PATENT DOCUMENTS 58-132081 8/1983 Japan .
58-173022 10/1983 Japan .

OTHER PUBLICATIONS

Chem. Abstr. 100:36923a (1984) Abstr. of Jpn. 58–132081.
English Synopsis of the Japanese Patent Application Laid–Open No. 58–173 022.
English Synopsis of the Japanese Patent Application Laid–Open No. 58–132 081.

*Primary Examiner*—Curtis R. Davis
*Attorney, Agent, or Firm*—Flynn, Thiel, Boutell & Tanis

[57] ABSTRACT

The present invention is concerned with a method of thermally decomposing a hydrocarbon and a thermal decomposition tube used therefor. A plurality of spiral fins are formed on the inner wall surface of the thermal decomposition tube. Since no-fin portions are formed on portions of the inner wall surface, the flow of a hydrocarbon through the no-fin portions is made turbulent to a suitable degree. For this reason, coke is prevented from adhering to the inner wall surface of the thermal decomposition tube.

15 Claims, 2 Drawing Sheets

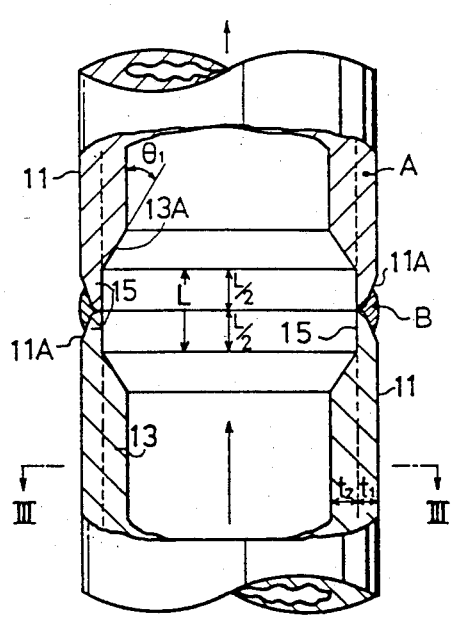
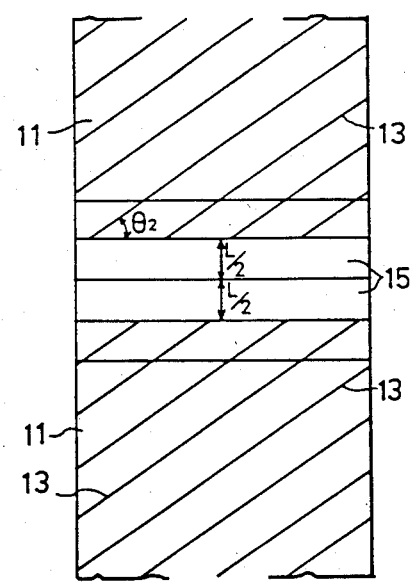
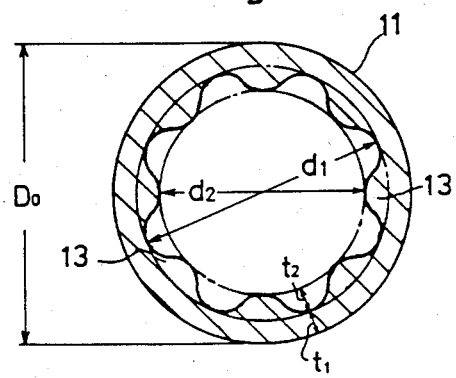

METHOD OF THERMALLY DECOMPOSING HYDROCARBON AND THERMAL DECOMPOSITION TUBE

BACKGROUND OF THE INVENTION

1. Field of the Invention

This invention relates to improvements in a method of thermally decomposing a hydrocarbon, wherein useful olefins such as ethylene and propylene are manufactured by thermally decomposing a hydrocarbon, and in a construction of a thermal decomposition tube.

2. Description of the Related Art

In general, for manufacturing olefin, particularly, ethylene by thermally decomposing hydrocarbons, there has been adopted such a method that a thermal decomposition furnace incorporating therein thermal decomposition tubes is used, a hydrocarbon is heated to a predetermined temperature to be thermally decomposed, and thereafter, quenched. In this case, in order to increase the heat transfer rate to a fluid in the thermal decomposition tubes, such various contrivances have been made such that fins or raised portions are provided on the inner surfaces or the outer surfaces of the thermal decomposition tubes, and the tubes are formed to have elliptical sectional configurations. In order to improve the yield of an olefin, and particularly, the yield of useful ethylene, such contrivances have been made so that the residence time in the thermal decomposition tubes are shortened, and cooled as quick as possible and so on.

However, if the reaction conditions are made too severe to improve the degree of conversion, then the adhesion of the produced coke to the interior of the thermal decomposition tubes becomes notable and the necessity of frequently performing operations of removing the adhering coke occurs. Heretofore, the efficiency of the method of thermal decomposition as a whole has not been improved.

With respect to the thermal decomposition tubes, there has been known that in order to raise the heat transfer rate in the tube, a metal tube provided on the inner surface thereof with spiral fins is useful as a thermal decomposition tube in an apparatus for thermally decomposing hydrocarbons (Japanese Patent Kokai (Laid-Open) Nos. 58-132081 and 58-173022).

However, since the thermal decomposition tube for hydrocarbons is used under particularly severe conditions, the adhesion of the produced coke is heavy, thus presenting such disadvantages that, in order to secure a given operating efficiency, coke must be frequently removed, which is found to be too troublesome.

To manufacture a metal tube having a predetermined length in more then one structure, it is technically difficult from the viewpoint of the manufacturing technology and the like in that a number of metal tubes should necessarily be connected to each other by welding. However, it is difficult to butt-weld these metal tubes with the end faces of the fins perfectly coinciding with each other, thus causing a problem of coke notably adhering to the portions of the fins that do not perfectly coincide with each other, thereby lowering the operating efficiency.

However, heretofore, the fact has been that the shape and the like of the thermal decomposition tube were not studied in detail.

SUMMARY OF THE INVENTION

One object of the present invention is to provide a method of thermally decomposing hydrocarbons, wherein the deposition of coke in the thermal decomposition tube is low, to thereby improve the operating efficiency of a thermal decomposition apparatus as a whole, and a thermal cracking tube therein.

In the method according to the present invention, wherein a metal tube, provided on the inner wall surface thereof with fins, is used as a thermal decomposition tube, and a hydrocarbon is made to flow through the metal tube to thereby thermally decompose, portions of the fins are cut away at a predetermined angle to form no-fin portions and the hydrocarbon is made to flow through the thermal decomposition tube.

To this end, in short, the present invention is based on the fact that in thermal decomposition tube provided on the inner surface thereof with fins, coke notably adheres onto the inner wall surface, contemplates a method, wherein no-fin portions are provided on the inner wall surface of the thermal decomposition tube, whereby the flow of the fluid is made to be turbulent to a suitable degree, so that coke is prevented from adhering.

As the types of hydrocarbons applicable to the method according to the present invention, there are listed hydrocarbons from naphtha to heavy gas oil, and further, gaseous aliphatic hydrocarbons, whereby useful olefins such as ethylene can be manufactured.

The thermal decomposition tube according to the present invention is constructed such that, particularly at portions where the metal tubes are connected to each other, portions of the fins are cut away at a predetermined angle to form no-fin portions, whereby the necessity of the difficult work of butt-welding between the fin end faces, when the metal tubes are connected to each other, can be eliminated, and the problem of the adhesion of coke, which appears at the connected portions between the metal tubes where the end faces of fins cannot be perfectly coincidentally connected to each other, can be solved by making the flow of the fluid be turbulent to a suitable degree, so that the efficiency of the thermal decomposition of the hydrocarbon can be improved.

The thermal decomposition furnace used according to the present invention may be any type of ordinary thermal decomposition furnace. A multiple tube type thermal decomposition furnace is preferable because it has no curved tube portions.

BRIEF DESCRIPTION OF THE DRAWINGS

FIG. 2 is a sectional view showing the essential portions of a metal tube used in a thermal decomposition tube of the above-mentioned apparatus;

FIG. 3 is an unfolded view of the metal tube; and

FIG. 4 is a sectional view taken along the line III—III in FIG. 2.

DESCRIPTION OF THE PREFERRED EMBODIMENT

Figure 1:
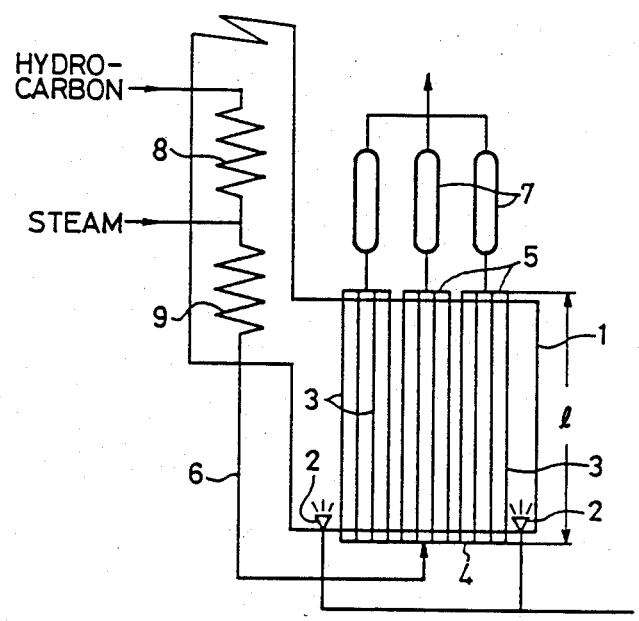
FIG. 1 is the outline of the arrangement of a thermal decomposition apparatus embodying the present invention.

One embodiment of the present invention will hereunder be described with reference to the accompanying drawings.

FIG. 1 shows the outline of the arrangement of the thermal decomposition apparatus used in this embodiment. Referring to this drawing, a thermal decomposition furnace 1 has burners 2 and twelve straight tube type thermal decomposition tubes 3. Inlets of these thermal decomposition tubes 3 are connected to inlet headers 4, outlets thereof are connected to outlet headers 5, the inlet headers 4 are connected thereto with a material feed tube 6, and the outlet headers 5 are connected thereto with quenching devices 7, respectively, outside the furnace.

The material feed tube 6 is supplied thereinto with hydrocarbon and stream, these materials are preheated by preheaters 8 and 9, respectively, and thereafter, fed to the inlet headers 4.

The thermal decomposition tube 3 may be any one in which portions of the fins are cut away at a predetermined angle of cut-away to form non-fin portions 15. The flow of the hydrocarbon is made turbulent by forming these no-fin portions 15, thus resulting in the decreased adhesion of coke and improved efficiency of thermal decomposition of the hydrocarbon. Incidentally, the turbulence referred to herein is a concept relative to the regulated flow of the hydrocarbon by the spiral fins.

As the method of manufacturing the thermal decomposition tube, various methods such as a method of manufacturing by fusion, a method of cold drawing and the like may be applied. A metal tube having a suitable length may be manufactured by these methods. According to the present invention, it is desirable to use a metal tube wherein predetermined no-fin portions are provided at a plurality of positions spaced 3–10 m apart from each other, and particularly at positions where the metal tubes are connected to each other. FIG. 2 shows an example in which two metal tubes 11 are welded to each other in the axial directions thereof to form the metal tube having the suitable length. These metal tubes 11 are formed of a nickel-chromium alloy for example, and each integrally provided on the inner peripheral surface thereof with a plurality of fins 13 each having a semicircularly arcuate configuration. As shown in FIG. 4, eight rows of the fins 13 are formed at regular intervals in the circumferential direction of the metal tube 11, each have a wave-shaped sectional configuration, and as shown in FIG. 3, are formed into a helical shape, extending out at an angle of inclination $\theta_2$ inclined to a line perpendicularly intersecting the longitudinal direction of the metal tube 11 when this line is referenced from.

It is preferable that this angle of inclination $\theta_2$ is 5°–20°, and particularly, 7°–15°. This is because, if this angle of inclination is 5° or therebelow, then, provision of helical grooves is not satisfactory in effect, while, if this angle of inclination exceeds 20°, then, pressure loss in the tube is undesirably increased. The fin 13 is formed such that, as indicated in the aforesaid Patent kokai (Laid-Open) No. 58-173022 for example, when the metal tube 11 is hot-extruded, straight fins are previously formed on the inner surface of the metal tube 11, and thereafter, the metal tube 11 is subjected to twisting in the circumferential direction thereof.

The end portions to be abutted against each other of the metal tube 11 are formed to provide beveling portions 11A where the outer diameter of the metal tube 11 is reduced by two steps, whereby the surfaces to be abutted against each other of the metal tube 11 are welded together wholly, so that firm connection can be achieved. In this case, the aforesaid beveling portion 11A may be formed at least at an end portion of either one of the metal tubes. An end portion of the fin 13 is cut away at an angle of cut-away $\theta_1$ from a position slightly inwardly of the end edge of the metal tube 11, the end edge is formed into a slanted portion 13A coinciding with the inner diametrical surface of the metal tube 11, and a predetermined length L from the end edge of the slanted portion 13A to the end edge of the metal tube 11 is a no-fin portion 15. In this case, the angle of cut-away $\theta_1$ is determined to be 75° or therebelow, and preferable to be within a scope of 8°–30° in particular, from the viewpoint of obtaining a proper flowing state of the fluid. If the angle of cut-away $\theta_1$ is higher than 75°, then the flow of the fluid is made more turbulent than necessary, and the adhesion of the coke is accelerated, thus undesirably causing the corrosion of the tube. It is preferable that the length L of the no-fin portion 15 is a length obtained in accordance with a formula:

$$(t_2/t_1) \times 10 \leq L \leq (t_2/t_1) \times 200$$

where $t_1$ represents a wall thickness of the metal tube 11 where no fin is formed, and $t_2$ represents the height of the fin 13. In this case, if the length L of the no-fin portion 15 is shorter than $(t_2/t_1) \times 10$, then the effect of preventing the coke from adhering is low and the welding of the metal tubes 11 is difficult. Whereas, if the length L is longer than $(t_2/t_1) \times 200$, then, when hydrocarbons, and the like, of high temperature are made to flow through the metal tubes 11 after welding, the turbulence of the flow becomes excessively high and the welded portions become partially high in temperature, whereby so-called hot spots are undesirably brought about.

Incidentally, as a preferred example of the metal tube 11, there may be exemplified one having the outer diameter=40–60 mm, the diameter of root of the fin $d_1$=25–45 mm, the diameter of crest of the fin $d_2$=13–35 mm, the wall thickness $t_1$=3–10 mm, the height of the fin $t_2$=3–10 mm, the number of the fins=5–10, the fin pitch=300–500 mm, the length of the cut-away portion L=100–350 mm, the angle of cut-away $\theta_1$=8°–30°, and the interval between the cut-away portions=4–8 m.

In welding the metal tubes 11 to each other, as shown in FIG. 2, beveling portions 11A are formed at the end portions of two metal tubes 11, the beveling portions 11A are abutted against each other in such a manner that the fins 13 are aligned on one and the same extension as shown in FIG. 3. In this case, the end edge of the fin 13 in the metal tube 11 is positioned inwardly of the end edge of the metal tube 11 by the length L/2 of the no-fin portion 15 through the slanted portion 13A, so that the abutting of the metal tubes against each other can be sufficiently made only if the beveling portions 11A are abutted against each other.

Subsequently, the beveling portions 11A are welded to each other by arc welding, gas welding or the like, whereby the connection between the metal tubes 11 is completed.

This embodiment as described above can offer the following advantages.

More specifically, the metal tubes 11 are formed with the no-fin portion 15 and used as the thermal decomposition tube, so that coke can be prevented from adhering to the welded portions the, necessity of frequently removing coke can be eliminated, and the operating efficiency of the thermal decomposition apparatus as a whole can be improved.

The end portion of the fin 13 is formed to provide the slanted portion 13A having the predetermined angle of cut-away $\theta_1$, so that the fluid in the metal tubes 11 can flow smoothly, and adhesion of coke to the slanted portions 13A can be avoided.

Moreover, in butt-welding the metal tubes 11 to each other, the necessity of strict positioning work, as in conventional welding of tubes having fins to each other, is eliminated, so that the thermal decomposition tube can be manufactured in a simplified manner.

The present invention will be specifically described in conjunction with an example of the following experiment using the thermal decomposition apparatus for hydrocarbons as shown below.

The thermal decomposition tube 3 used in the above thermal decomposition apparatus was formed of a nickel-chromium alloy and had an outer diameter $D_0=49.7$ mm, the inside diameter at the base of the fin $d_1=36.2$ mm, the inside diameter at the crest of the fin $d_2=24.2$ mm, the wall thickness $t_1=6.0$ mm, the height of the fin $t_2=6.0$ mm, the number of the fins=8, the fin pitch=400 mm and the length of the thermal decomposition tube $l=11$ m. As the hydrocarbon material, naphtha was used, and the thermal decomposition was performed under the conditions of steam/hydrocarbon weight ratio=0.5, the inlet temperature of the thermal decomposition tube 3=600° C., the inlet pressure=2.0 kg/cm²G, the outlet temperature of the thermal decomposition tube=880° C., the outlet pressure=1.0 kg/cm²G, the residence time 100 milliseconds, to thereby obtain a product having a main component of ethylene.

The thermal decomposition tube 3 was constructed such that two metal tubes 11 each having the length of 5.5 m were welded to each other. As the conditions of welding, four groups were adopted. Group 1 had the conditions in welding of the length of cut-away portion $L=0$ mm and the angle of cut-away $\theta_1=15°$, Group 2 has the conditions of $L=220$ mm, and $\theta_1=15°$, Group 3 had the conditions of $L=30$ mm and $\theta_1=80°$, and Group 4 had the conditions of having no cut-away portions. Here, Group 1 was under the conditions of the present invention.

The following Table shows the results.

TABLE

| | TEMPERATURE IMMEDIATELY AFTER START OF OPERATION | | TEMPERATURE AFTER 20 DAYS' OPERATION | |
|---|---|---|---|---|
| | POSITION A | POSITION B | POSITION A | POSITION B |
| GROUP 1 | 1000° C. | 1000° C. | 1040° C. | 1040° C. |
| GROUP 2 | 1000° C. | 1015° C. | 1040° C. | 1070° C. |
| GROUP 3 | 1000° C. | 1000° C. | 1050° C. | 1040° C. |
| GROUP 4 | 1000° C. | 1000° C. | 1060° C. | 1040° C. |

POSITION A: 500 mm downstream from the abutment between the metal tubes
POSITION B: 10 mm downstream from the abutment between the metal tubes As apparent from the above example of experiments, the welding method of Group 2 is adopted, it is known that the welding portion becomes a hot spot, whereby the coking rate is high. Groups 3 and 4 are not problematical in temperature. However, since Group 3 has the large angle of cut-away $\theta_1$ and Group 4 has no cut-away portions, the flow at the downstream of the welding portion is made turbulent to a considerable extent, whereby coking at the downstream is accelerated, thus presenting a problem in practice.

In working, the section of the fin need not necessarily be a convex shape, and may be a square shape or the like. The material of the metal tube 11 need not necessarily be the nickel-chromium alloy, and may be formed of any of other metallic materials.

The thermal decomposition tube 3 has been constructed such that the two metal tubes 11 are welded to each other, however, the number of the metal tubes is to be determined in accordance with the length of the thermal decomposition tube, and the respective welded portions are each formed with the no-fin portion 15.

The present invention with the above-described arrangement is advantageous in providing a method of thermally decomposing hydrocarbon, wherein deposition of coke in the thermal decomposition tube is low, so that the operating efficiency of the thermal decomposition apparatus as a whole can be improved.

What is claimed is:

1. In a method of thermally decomposing a hydrocarbon by flowing said hydrocarbon through a thermal decomposition tube having fins provided an an inner wall surface thereof, said thermal decomposition tube comprising a plurality of metal tubes connected to each other at their end faces, the improvement comprising utilizing a thermal decomposition tube having no-fin sections formed on the inner wall surface where said plurality of metal tubes are connected to each other, said no-fin sections being formed by the fins being cut away at an angle of $\theta_1$ of 75° or less.

2. A method of thermally decomposing a hydrocarbon as set forth in claim 1, wherein, when the wall thickness of a no-fin section is $t_1$ and the height of the fin is $t_2$, the length L of the no-fin section is $$(t_2/t_1) \times 10 \leq L \leq (t_2/t_1) \times 200.$$

3. A method of thermally decomposing a hydrocarbon as set forth in claim 1, wherein the angle of cut-away $\theta_1$ of said fin is $$8° \leq \theta_1 \leq 30°.$$

4. A method of thermally decomposing a hydrocarbon as set forth in claim 1, wherein said fins are formed into helixes.

5. A method of thermally decomposing a hydrocarbon as set forth in claim 4, wherein a reference line perpendicularly intersecting the longitudinal axis of said thermal decomposition tube forms an angle of inclination with the helixes of said fin of 5°–20°.

6. A method of thermally decomposing a hydrocarbon as set forth in claim 1, wherein said plurality of metal tubes are made of a nickel-chromium alloy.

7. A thermal decomposition tube for thermally decomposing a hydrocarbon comprising a plurality of metal tubes connected to each other at their end faces, said plurality of metal tubes having fins and no-fin sections formed on an inner wall surface thereof, said no-fin sections being formed by the fins being cut away at an angle $\theta_1$ of 75° or less on the inner wall surface where said plurality of metal tubes are joined to each other.

8. A thermal decomposition tube as set forth in claim 7, wherein, when the wall thickness of a no-fin section is $t_1$ and the height of the fin is $t_2$, the length L of the no-fin section is determined to be:

$(t_2/t_1) \times 10 \leq L \leq (t_2/t_1) \times 200.$

9. A thermal decomposition tube as set forth in claim 7, wherein the angle of cut-away $\theta_1$ of said fin is $8° \leq \theta_1 \leq 30°.$ 10. A thermal decomposition tube as set forth in claim 7, wherein said fins are formed into helixes.

11. A thermal decomposition tube as set forth in claim 7, wherein the wall thickness of an end portion of at least one of said plurality of metal tubes at a portion, where said plurality of metal tubes are connected to each other, is progressively decreased.

12. A thermal decomposition tube as set forth in claim 10, wherein said fins have sectional shapes of waves.

13. A thermal decomposition tube as set forth in claim 10, wherein the number of said fins is 5–10, said fins being provided along the circumferential direction in said thermal decomposition tube.

14. A thermal decomposition tube as set forth in claim 10, wherein a reference line perpendicularly intersecting the longitudinal axis of said thermal decomposition tube forms an angle of inclination with the helixes of said fin of 5°–20°.

15. A thermal decomposition tube as set forth in claim 7, wherein said plurality of metal tubes are made of a nickel-chromium alloy.

* * * * *